(12) United States Patent
Aebi et al.

(10) Patent No.: US 8,388,686 B2
(45) Date of Patent: Mar. 5, 2013

(54) INTERVERTEBRAL IMPLANT WITH TILTABLE JOINT PARTS

(76) Inventors: Max Aebi, Bern (CH); Dominique Burkard, Gretzenbach (CH); Robert Frigg, Bettlach (CH); Beat Lechmann, Bettlach (CH); Robert Mathys, Jr., Bettlach (CH); Paul Pavlov, Nijmegen (NL)

( * ) Notice: Subject to any disclaimer, the term of this patent is extended or adjusted under 35 U.S.C. 154(b) by 1532 days.

(21) Appl. No.: 10/539,660

(22) PCT Filed: Dec. 17, 2002

(86) PCT No.: PCT/CH02/00705
§ 371 (c)(1),
(2), (4) Date: Jan. 18, 2007

(87) PCT Pub. No.: WO2004/054476
PCT Pub. Date: Jul. 1, 2004

(65) Prior Publication Data
US 2007/0276498 A1    Nov. 29, 2007

(51) Int. Cl.
*A61F 2/44* (2006.01)
(52) U.S. Cl. .................... 623/17.15; 623/17.16
(58) Field of Classification Search .......... 606/279; 623/17.11–17.16, 23.39, 23.41–23.42, 48; 33/495–500; 403/350–352, 409.1, 79, 91, 403/95, 113, 119, 121
See application file for complete search history.

(56) References Cited

U.S. PATENT DOCUMENTS

| | | | |
|---|---|---|---|
| 4,759,769 A * | 7/1988 | Hedman et al. ............ | 623/17.13 |
| 5,593,447 A * | 1/1997 | Angeli ........................ | 623/22.43 |
| 5,893,889 A | 4/1999 | Harrington | |
| 6,440,168 B1 | 8/2002 | Cauthen | |
| 6,610,093 B1 * | 8/2003 | Pisharodi ................... | 623/17.15 |
| 7,179,294 B2 * | 2/2007 | Eisermann et al. ........ | 623/17.15 |
| 7,273,496 B2 * | 9/2007 | Mitchell .................... | 623/17.14 |
| 2002/0052656 A1 * | 5/2002 | Michelson ................ | 623/17.11 |
| 2004/0143332 A1 * | 7/2004 | Krueger et al. ............ | 623/17.14 |

FOREIGN PATENT DOCUMENTS
CA    2332822    11/1999

OTHER PUBLICATIONS
WO 02/089701, Intervertebral Disc Prosthesis and Fitting Tools, Publication Date: Nov. 14, 2002.

* cited by examiner

*Primary Examiner* — Kevin T Truong
*Assistant Examiner* — Larry E Waggle, Jr.
(74) *Attorney, Agent, or Firm* — Woodcock Washburn LLP (57) ABSTRACT

An intervertebral implant (1) including an upper section (10) provided with a ventral side area (11), a dorsal side area (12), two lateral side areas (13, 14), a top apposition surface (15) and a bottom surface (16), a lower section (20) provided with a ventral side area (21), a dorsal side area (22), two lateral side areas (23,24), a bottom apposition surface (25) and a top surface (26). The two sections (10,20) are moveable in relation to each other by means of two joints (38;39) arranged between the two sections (10;20), wherein each of the joints (38;39) has a swivel axis (3;4) and the two swivel axes (3;4) are arranged perpendicular to each other, and each joint (38; 39) comprises a first joint section (31;32;33) with an elevation (49;50) provided with an edge (51;53) for the bearing of a second joint section (31;32;33) in a way that allows titling around the swivel axis (3;4).

20 Claims, 5 Drawing Sheets

INTERVERTEBRAL IMPLANT WITH TILTABLE JOINT PARTS

BACKGROUND OF THE INVENTION

The invention relates to an intervertebral implant according to the generic term of Patent Claim 1 and to a process for the replacement of a defect, natural intervertebral disk by an intervertebral implant according to.

After removal of a damaged, natural intervertebral disk or a damaged nucleus pulposus of an intervertebral disk, implants or prostheses are inserted into the intervertebral space of two neighbouring vertebral bodies. This suggests the idea of restoring the situation as much as possible to a natural state, i.e. specifically to restore the original height of the intervertebral disk and thus the original distance between the two neighbouring vertebral bodies. Furthermore, the patient should be able to carry out movements of the neighbouring vertebral bodies relative to each other in the natural way, thereby incurring as little obstruction as possible. This essential feature of this system is its ability to retain the freedom of movement in forward/reverse inclination, i.e. flexion and extension of the vertebral bodies, and in lateral bending of the vertebral bodies within the natural limits. The natural sinews and muscles along the spinal column are in general left intact so that they further stabilise the movements of a mechanical intervertebral disk prosthesis.

A characteristic intervertebral disk endoprosthesis is state of the art from DE-A 35 29 761 BÜTTNER. This known intervertebral disk endoprosthesis basically consists of two symmetric closing plates with concave sliding surfaces facing each other, and each having an external surface for laying on the base plate, or the cover plate of the adjoining vertebral body, and a distance piece positioned between the closing plates with convex sliding surfaces arranged complementary to the concave sliding surfaces on the closing plates. The sliding surfaces are designed in one embodiment as section surfaces of a cylinder coat area, wherein the sliding surfaces arranged on the two closing plates are provided complementary to each of the adjoining sliding surfaces at the distance piece, and two complementary sliding surfaces form the articulation surfaces, which can be moved towards each other, of a joint element rotating around a swivel axle. The joint comprises an upper and a lower joint element, each of which has one swivel axle. The two swivel axles are set at 90° to each other. The disadvantages of this known intervertebral disk endoprosthesis is that a) the arrangement of an intervertebral disk endoprosthesis with only one fulcrum does not take sufficient account of the overlaying swivel movements transferred by the natural intervertebral disk, specifically in the case of anterior-posterior and in lateral flexion, which in the natural intervertebral disk are independent of each other;

b) the vertebral joint is put under strain by swivel movements, specifically with translation in the anterior-posterior direction (face joint), which could cause pain for the patient;

c) disadvantageous friction forces are generated by two articulating surfaces sliding on each other. This also leads to wear on the surfaces, including also abrasion and resistance in movement of the joint elements. There is also the risk of the "stick slip" effect;

d) a mechanical intervertebral disk prosthesis can scarcely prevent the further degeneration of the affected movement segments. Restoration of the original freedom of movement significantly reduces pain, with the resulting improvement to the patient's quality of life. A review of treatment will, however, have to be undertaken if pain recommences. This will normally involve complete removal of an intervertebral disk prosthesis of the standard model and a stiffening of the movement segment. This operation represents extreme discomfort and strain on the patient; and e) the form of contact areas to the neighbouring vertebral bodies is generally not taken into account. The conventional types of intervertebral disk prosthesis implants have flat contact areas, which are often supplemented with keel-type elevations.

BRIEF SUMMARY OF THE INVENTION

The invention is intended to remedy this situation. The invention is based on the task of creating an intervertebral implant that comprises a joint, the axles of which are provided with bearings with minimum friction.

The invention solves the task with an intervertebral implant and with a process for replacing a defect, natural intervertebral disk by an intervertebral implant.

The advantages achieved by the invention can generally be seen in that with the intervertebral implant according to the invention the swivel movements in anterior-posterior and lateral direction are independent of each other;

the friction surface of the movements on blade-like means is reduced to a minimum; and the line contact between the joint sections instead of sliding surfaces reduces the friction forces in the joint and as a result relative movement among the vertebral bodies, specifically lateral bending and flexion/extension movement of the spinal column is not impaired.

Due to the different positions of the natural swivel axes in the different intervertebral disk spaces along the spinal column the arrangement of the swivel axes can be warped or intersecting.

The length of the blades leads to a stabilising of the joints against the two sections turning around the central axis. The flank angles of the elevations measure preferably between 1° and 30° whereas the flank angles of the depressions measure preferably between 6° and 70°.

In a preferred embodiment of the intervertebral implant according to the invention, the implant comprises two joints, each of which is designed with a first and a second joint section, wherein the second joint section is provided with a depression for receiving a wedge member on the first joint section that can be tilted around the swivel axis. This achieves the advantage that no translation movements of the vertebral bodies adjoining the implant are permitted, which relieves strain on the face joints.

In a further embodiment of the intervertebral implant according to the invention, a means can be attached to the two sections from the ventral side areas which fixes the two sections ventral at a specific distance relative to each other. This measure provides the advantage that the two sections for insertion into the intervertebral space can be brought to a position with fixed height and can be moved around the joint after insertion into the intervertebral space and can be placed on the base or cover plate of the adjoining vertebral body.

In a further embodiment of the intervertebral implant according to the invention, the means allows temporary blocking of the mobility of the two sections around the joint. This measure provides the advantage that the joint integrated in the intervertebral space can be blocked by a minimum invasive operation. This is particularly advantageous in cases where the patient suffers from post-operative pain, i.e. where degeneration of the affected spinal column segment continues and the surgeon is considering a fusion of the affected vertebra. The means can preferably be attached to the two ventral side areas of the two sections. With this subsequent, secondary blocking of the mobility of the two sections around the joint, the intervertebral implant is stiffened and transferred to an arthrodesis implant (fusion cage).

In a further embodiment of the intervertebral implant according to the invention, the means comprises an insert, which can be placed into each depression on the surfaces of the upper and lower section opposite each other. These depressions are preferably provided as dovetail guides that are open on the ventral side areas, so that the ends of the insert arranged complementary to the dovetail guides can be inserted from ventral into the dovetail guides. This provides the advantage that the mobility of the two sections around the joint is blocked due to the positioning of the insert. The rigidity of the blocking can be increased when the dovetail guides are designed so that they are reduced is size towards the central axis of the intervertebral implant, which creates additional wedging of the insert in the dovetail guides.

In a further embodiment of the intervertebral implant according to the invention, the two sections are provided with drill holes for receiving the bone fixation means, specifically bone screws, wherein the drill holes are provided with longitudinal axes that stand perpendicular to the central axis. Preferably two drill holes will pass through one of the two sections from the ventral side area to the apposition surface. The longitudinal axes, if only an axial fixing of the intervertebral implant is provided, will then be able to stand only perpendicular to the central axis from a lateral perspective, or, if fixing of the intervertebral implant with stable angle is provided, will also from a lateral perspective diverge from the inner surfaces of the two sections against the apposition surfaces.

In a further embodiment of the intervertebral implant according to the invention, the drill holes for receiving the bone fixation means are provided with internal threads, which allows additional, rigid fixing of the bone fixation means in the two sections. The drill holes preferably have a conical shape so that a stronger fixing of the bone fixation means to each of the two sections can be achieved by the resulting conical thread connections between the internal threads and the external threads on the heads of the bone fixation means.

The apposition surfaces are preferably of convex shape and provided with a three-dimensional structure, preferably in the form of pyramid elevations. This arrangement of the apposition surfaces takes account of the anatomy of the vertebral body end plates.

The process according to the invention is intended primarily for replacing a defect, natural intervertebral disk by an intervertebral implant and comprises the following steps:
A) blocking of the joint(s) of an intervertebral implant by means of a special device placed in a certain position of the joint(s);
B) insertion of the intervertebral implant into the intervertebral space to be treated;
C) release and removal of the device inserted into the intervertebral implant for blocking the joint(s). Blocking the joint provides the advantage that the moveable sections with the external apposition surfaces can be inserted more easily into the intervertebral space to be treated.

In a further application of the process according to the invention, this comprises the subsequent blocking of the joint (s) on the implanted intervertebral implant by means of the device intended for blocking the joint(s). This provides the advantage that if the patient should suffer from post-operative pains or in case of a further degeneration of the movement segment, the joint(s) on the intervertebral implant are blocked post-operative by the insertion of the means intended for this purpose. This subsequent blocking can be achieved with an minimally invasive, preferably a laparoscopic operation. The intervertebral implant then assumes the function of a cage, so that the affected movement segment of the spinal column can be stiffened.

The invention and refinements of the invention are described in more detail below on the basis of a partially schematic illustration of several embodiments.

DETAILED DESCRIPTION OF THE INVENTION

Figure 1:
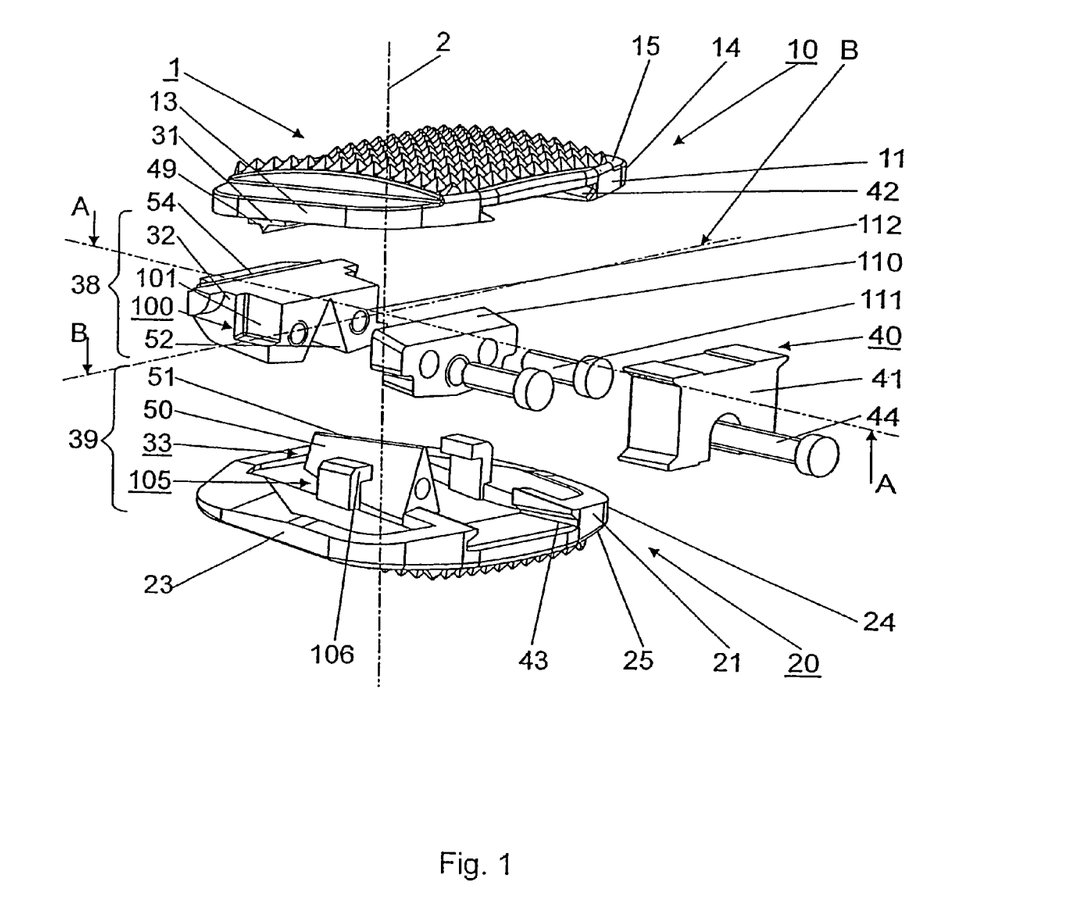
FIG. 1 shows an explosion diagram of one embodiment of the intervertebral implant according to the invention.
Figure 2:
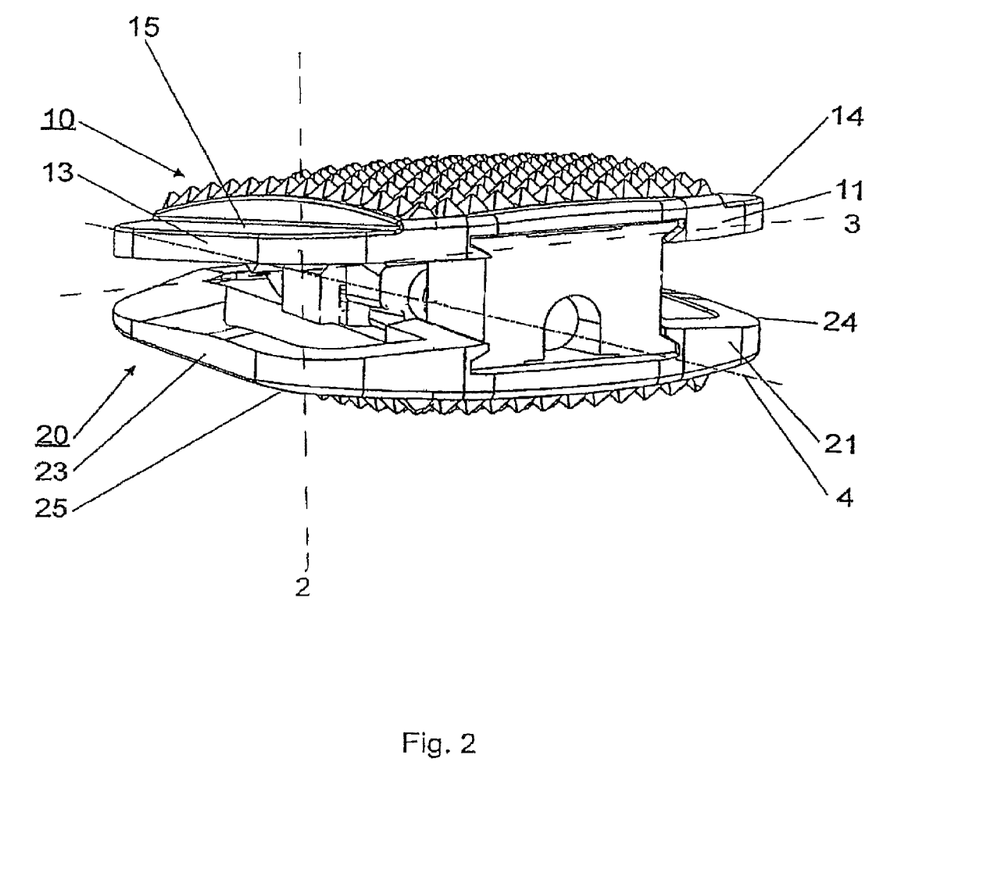
FIG. 2 shows a perspective view of the embodiment of the intervertebral implant according to the invention shown in FIG. 1 in assembled state.

FIG. 1 and FIG. 2 show an embodiment of the intervertebral implant 1 according to the invention, which comprises an upper section 10 with a top apposition surface 15 arranged perpendicular to the central axis 2 for laying on the base plate of an adjoining vertebral body, a lower section 20 with a lower apposition surface 25 arranged perpendicular to the central axis 2 for laying on the cover plate of the adjoining vertebral body and two joints 38;39. The upper section 10 further including a ventral side area 11, a dorsal side area 12, two lateral side areas 13, 14, and a bottom surface 16. The lower section further including a ventral side area 21, a dorsal side area 22, two lateral side areas 23,24, and a top surface 26. The upper section 10 and the lower section 20 are connected with the joints 38;39 and moveable in relation to each other, whereby the mobility of the upper section 10 relative to the lower section 20 is restricted by a first swivel axle 3 arranged perpendicular to the central axis 2 within an angle range of +10 degrees to −6 degrees and by a second swivel axle 4 arranged perpendicular to the central axis 2 and vertical to the first swivel axle 3 within an angle range of .+−7 degrees.

The joints 38;39 are realised by three joint elements 31;32; 33, of which the lower joint element 33 and the upper joint element 31 each form a joint 38;39 interacting with the central joint element 32. The two joints 38;39 are provided in the form of rockers and are each provided with a swivel axis 3;4, wherein the swivel axes stand vertical to each other and vertical to the central axis 2. The lower joint 39 comprises a wedge member 50 connected to the lower section 20 and forming the lower joint section 33, and a depression 52 arranged in the central joint section 32 and accepting the wedge member 50. The wedge member is fitted with a pointed tip 51 forming the swivel axis 4, which is positioned in the depression 52 in such a way that the two joint sections 32;33 together form a joint 39 that can be tilted around the swivel axis 4 on the pointed tip 51. The upper joint 38 is similarly made up of a wedge member 49 arranged on the upper joint section 31 and parallel to the swivel axis 3 and a depression 54 arranged on the central joint section 32 and accepting the wedge member 49. The wedge member 49 is provided with a pointed tip 53 forming the swivel axis 3, which is carried in the depression 54 in such a way that the two joint sections 31;32 form a joint 38 that can be tilted around the swivel axis 3 on the pointed tip 53.

The mobility of the two sections 10;20 relative to each other can be blocked by the means 40 in a way that allows release. The means 40 comprises in the embodiment described here an insert 41 that can be slid in from the ventral side areas 11;21 of the two sections 10;20 perpendicular to the central axis 2 and parallel to the lateral side areas 13;14;23;24 of the two sections 10;20. The insert 41 is slid in two depressions 42;43, provided in the form of dovetail guides. The insert 41 is inserted from the ventral side areas 11;21 of the two sections 10;20 into the depressions 42;43 composed as dovetail guides and fitted to the lower section 20 by means of a screw 44. The insert 41 is furthermore arranged in the terminal state complementary to the depressions 42;43, so that the two sections 10;20 with fitted insert 41 are fixed relative to each other parallel to the central axis 2.

A first catching means 100 is also attached to the central joint section 32, which can be engaged with the second catching means 105 at the lower joint section 33 and which prevent the central joint section 32 being removed from the lower joint section 33 after the fixing element 110 has been secured to the central joint section 32. The securing of the fixing element 110 takes place by means of screws 111, which are inserted into the thread holes 112 beside the depression 52 in the central joint section 32. The first catching means 100 comprise depressions 101 on the central joint section 32, which can be engaged flush with the catches 106 of the second catching means 105. This operation prevents the two joint sections 32;33 from becoming separate from each other. There are furthermore hinges 120 (FIG. 5 and FIG. 6) arranged between the upper joint section 31 and the central joint section 32, by means of which the two joint sections 31;32 are held together parallel to the central axle 2 without this leading to any restriction in the rotation movement of the two joint sections 31;32 relative to each other around the first swivel axis 3.

Figure 3:
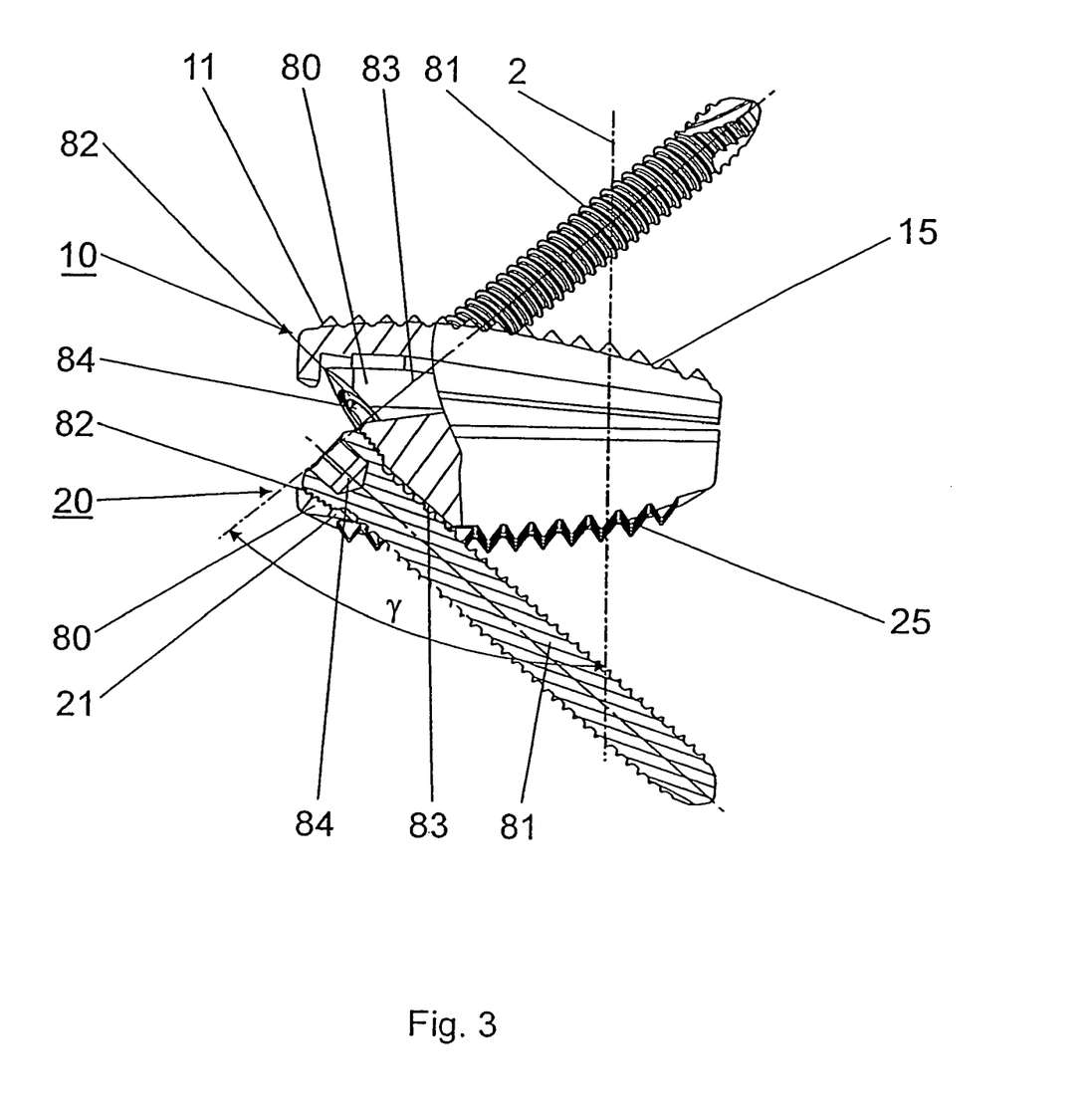
FIG. 3 shows a lateral view of a further embodiment of the intervertebral implant according to the invention.
Figure 4:
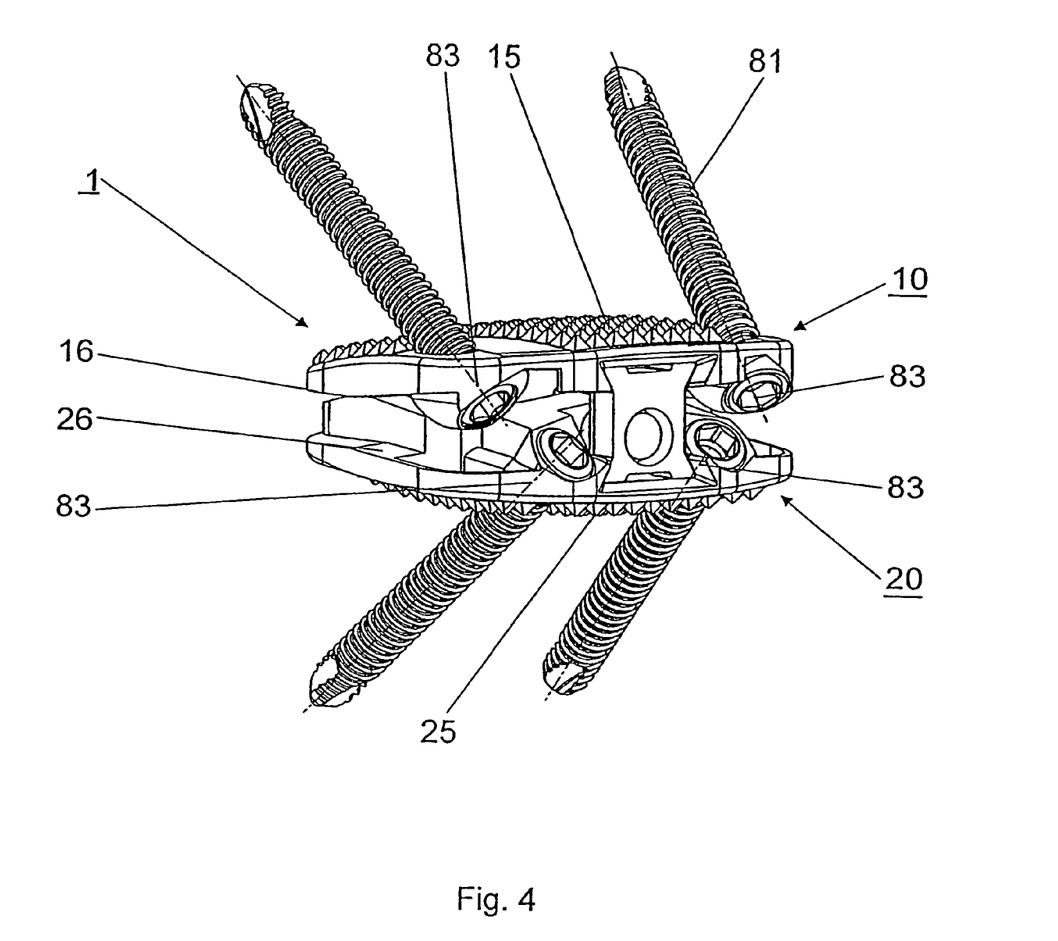
FIG. 4 shows a perspective view from ventral of the embodiment according to FIG. 3.

FIG. 3 illustrates an embodiment of the intervertebral implant 1 according to the invention, which differs from the embodiment illustrated in FIG. 1 and FIG. 2 only in that the two sections 10;20 also comprise drill holes 80 for receiving the bone fixation means 81, whereby the bone fixation means 80 is provided in this case as bone screws. The drill holes 80 are provided with longitudinal axes 83 that form an angle γ with the central axis 2. In addition, each two drill holes 80 (FIG. 4) run trough one of the two sections 10;20 from the ventral side area 11;21 to the apposition surface 15;25. The longitudinal axes 83 of the drill holes 80 are standing perpendicular to the central axis 2 both from a lateral (FIG. 3) and from a ventral (FIG. 4) point of view. The drill holes 80 are furthermore provided in conical design and tapering towards the apposition surfaces 15;25 and provided with internal threads 82 that are used for screwing reception of the screw heads 84 of the bone fixation device 81 realised here in the form of bone screws and provided with complementary external threads.

Figure 5:
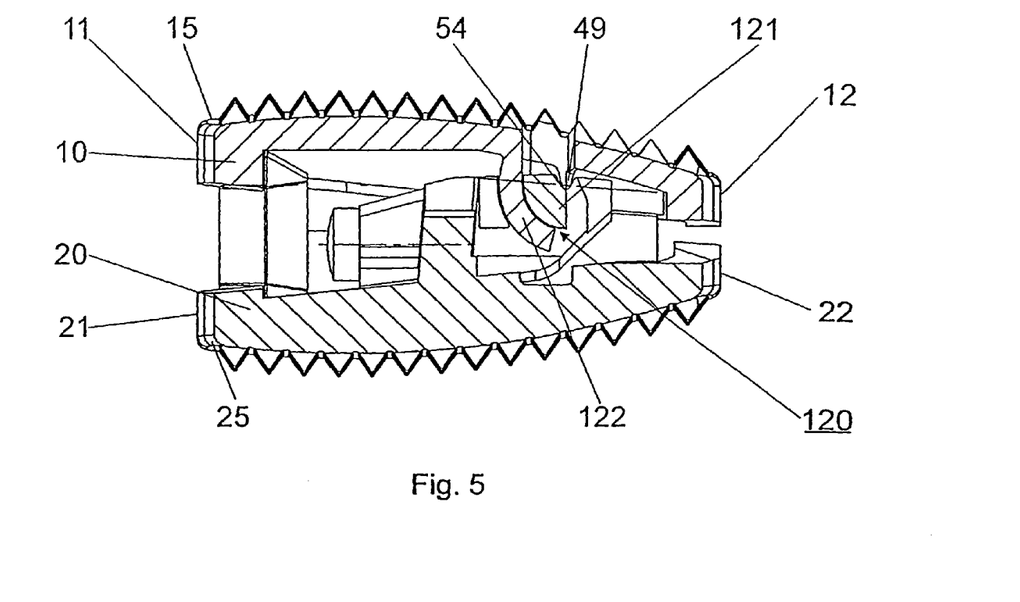
FIG. 5 shows a section along the line A-A in FIG. 1 with a lateral view.
Figure 6:
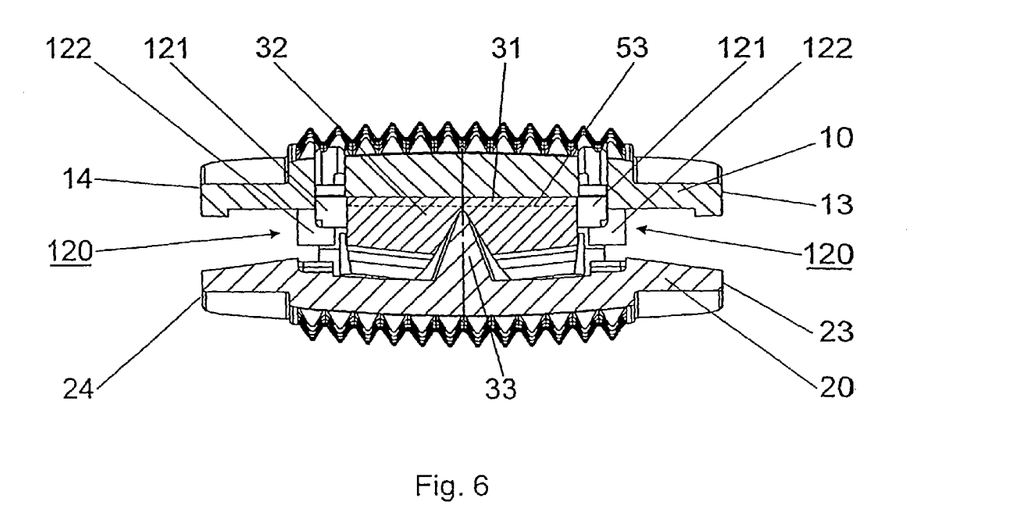
FIG. 6 shows a section along the line B-B in FIG. 1 with a dorsal view.

FIG. 5 and FIG. 6 show detailed illustrations of the two hinges 120 between the upper joint section 31 and the central joint section 32. The hinges 120 permit a relative swivel movement of the two joint sections 31;32 around the first swivel axis 3 (FIG. 2) formed by the pointed tip 53 on the second wedge member 49 and the depression 54, and comprise cams 121 attached laterally at the end on the central joint section 32, which cams are rounded towards the ventral side surfaces 11;21 of the intervertebral implant 1, and shells 122 attached to the upper joint section 31, which surround the rounded sides of the cams 121 from the direction of the ventral side surfaces 11;21 as a circular arc with an angle of approx. 90°. These shells 122 lead to the upper joint section 31 being secured parallel to the central axis 2 (FIG. 1) on the central joint section 32.

The invention claimed is:

1. An intervertebral implant comprising a central axis, an upper section, configured to contact the base plate of a vertebral body lying above, and a lower section configured to contact the cover plate of a vertebral body lying below, wherein:
   the upper section has a ventral side area, a dorsal side area, two lateral side areas, a top apposition surface, and a bottom surface;
   the lower section has a ventral side area, a dorsal side area, two lateral side areas, a bottom apposition surface, and a top surface; and
   the upper and lower sections are moveable in relation to each other via two joints arranged between the upper and lower sections, wherein:
   each of the joints has a swivel axis and the two swivel axes are arranged transversely or perpendicular to each other; and
   the two joints comprise an upper joint element connected with the upper section, a central joint element, and a lower joint element connected with the lower section, wherein:
   each joint comprises a wedge member having a tip that extends along a length of the wedge member, the tip configured to bear against the central joint element in a way that allows tilting around the respective swivel axis.

2. The intervertebral implant according to claim 1, wherein the tip is a pointed tip.

3. The intervertebral implant according to claim 2, wherein the central joint element comprises a pointed depression configured to receive the pointed tip on the upper section.

4. The intervertebral implant according to claim 3, wherein the wedge member formed on the lower section extends parallel to the swivel axis with the pointed tip forming the swivel axis, and wherein the pointed tip is carried in a pointed depression on the central joint element.

5. The intervertebral implant according to claim 3, wherein the wedge member formed on the upper section extends parallel to the swivel axis with the pointed tip forming the swivel axis, and wherein the pointed tip is carried in a pointed depression on the central joint element.

6. The intervertebral implant according to claim 1, wherein the swivel axes are warped in relation to each other.

7. The intervertebral implant according to claim 1, further comprising a means for keeping the two sections, measured at their ventral side areas, at a fixed distance from each other.

8. The intervertebral implant according to claim 1, further comprising a means for causing temporary blocking of the mobility of the two sections around the joints.

9. The intervertebral implant according to claim 7, wherein the means can be attached to the two ventral side areas of the two sections.

10. The intervertebral implant according to claim 8, wherein the means comprises an insert with a lower end and an upper end and a depression in the surfaces at each of the two sections, which are open on the ventral side areas, and that the insert with its ends can be inserted into each of the depressions.

11. The intervertebral implant according to claim 10, wherein the depressions are dovetail guides and the ends on the insert are arranged complementary to these dovetail guides.

12. The intervertebral implant according to claim 11, wherein the dovetail guides are tapered from the ventral side areas towards the dorsal side areas.

13. The intervertebral implant according to claim 1, wherein the upper and the lower sections each comprise at least two drill holes running through from the ventral side areas to the apposition surfaces with longitudinal axes configured to receive bone fixation devices.

14. The intervertebral implant according to claim 13, wherein the longitudinal axes of the drill holes make an angle γ with the central axis.

15. The intervertebral implant according to claim 14, wherein the angle γ lies in a range between 20 degrees and 65 degrees.

16. The intervertebral implant according to claim 13, wherein the longitudinal axes of the drill holes as seen from the ventral side areas diverge from the inner surfaces against the apposition surfaces.

17. The intervertebral implant according to claim 13, wherein the drill holes are conically tapered towards the apposition surfaces.

18. The intervertebral implant according to claim 13, wherein the drill holes have an internal thread.

19. The intervertebral implant according to claim 1, wherein the central joint element comprises a first catching means and the lower section comprises a second catching means, and that the first and second catching means can be engaged with each other.

20. The intervertebral implant according to claim 1, wherein hinges are attached between the upper section and the central joint element, through which the upper section and the central joint element are held together parallel to the central axis without this causing any restriction of the rotation movement of the upper section and the central joint element relative to each other around the respective swivel axis.

* * * * *

UNITED STATES PATENT AND TRADEMARK OFFICE
CERTIFICATE OF CORRECTION

PATENT NO. : 8,388,686 B2
APPLICATION NO. : 10/539660
DATED : March 5, 2013
INVENTOR(S) : Aebi et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2221 days.

Signed and Sealed this
First Day of September, 2015

Michelle K. Lee
*Director of the United States Patent and Trademark Office*